US008660641B2

(12) United States Patent
Kakei et al.

(10) Patent No.: US 8,660,641 B2
(45) Date of Patent: Feb. 25, 2014

(54) METHOD FOR IDENTIFYING AND EVALUATING PARALLEL MOTOR CONTROL FUNCTION IN THE BRAIN BASED ON ELECTROMYOGRAM SIGNALS

(75) Inventors: Shinji Kakei, Tokyo (JP); Jongho Lee, Tokyo (JP); Yasuhiro Kagamihara, Tokyo (JP)

(73) Assignees: Tokyo Metropolitan Institute of Medical Science, Tokyo (JP); Tokyo Metropolitan Government, Tokyo (JP)

( * ) Notice: Subject to any disclaimer, the term of this patent is extended or adjusted under 35 U.S.C. 154(b) by 543 days.

(21) Appl. No.: 12/807,861

(22) Filed: Sep. 15, 2010

(65) Prior Publication Data

US 2011/0213267 A1 Sep. 1, 2011

(30) Foreign Application Priority Data

Feb. 26, 2010 (JP) ................................. 2010-042301

(51) Int. Cl.
*A61B 5/0488* (2006.01)

(52) U.S. Cl.
USPC ......................................... 600/547; 600/546

(58) Field of Classification Search
USPC ................................................. 600/546, 547
See application file for complete search history.

(56) References Cited

U.S. PATENT DOCUMENTS

2011/0137196 A1* 6/2011 Kakei et al. ................... 600/546

FOREIGN PATENT DOCUMENTS

| JP | 2000-279463 A | 10/2000 |
| JP | 2002-514939 A | 5/2002 |
| JP | 2002-369818 A | 12/2002 |
| JP | 2005-185557 A | 7/2005 |

| WO | 96/20643 A1 | 7/1996 |
| WO | 2009/028221 A1 | 3/2009 |
| WO | WO 2009028221 A1 * | 3/2009 |

OTHER PUBLICATIONS

Kakei et al. "A new system for the quantitative evaluation of motor commands for neurorehabilitation" Brain Nerve Feb. 2010; 62(2): 151-63, english language abstract.*
Lee et al., Two modes of motor commands for tracking movement of the wrist (Poster), 32nd Annual Meeting of the Japan Neuroscience Society, Sep. 18, 2009.

* cited by examiner

*Primary Examiner* — Sean P Dougherty
*Assistant Examiner* — Michael C Stout
(74) *Attorney, Agent, or Firm* — McDermott Will & Emery LLP

(57) ABSTRACT

The present invention provides a system for evaluating motor control function in the brain. This system is for evaluating the motor control function in the brain of a subject from the electromyogram (EMG) data of joint prime movers and the data on the position, velocity and acceleration of the joint, wherein both of the data have been obtained by measuring a target-tracking movement performed by the subject with a motion measurement unit that tracks a moving target, the system comprising the following means (a) to (c):

(a) means for separating the frequencies of the EMG data and the frequencies of the data on the position, velocity and acceleration into a plurality of frequency components;
(b) means for determining the ratio of viscosity coefficient to elastic coefficient (B/K ratio) for each of the frequency components by applying the EMG data and the data on the position, velocity and acceleration to a specific movement equation; and
(c) means for evaluating the causal relationship between the motor control function in the brain and the target-tacking movement using the B/K ratio as an index.

10 Claims, 14 Drawing Sheets
(2 of 14 Drawing Sheet(s) Filed in Color)

FIG.3
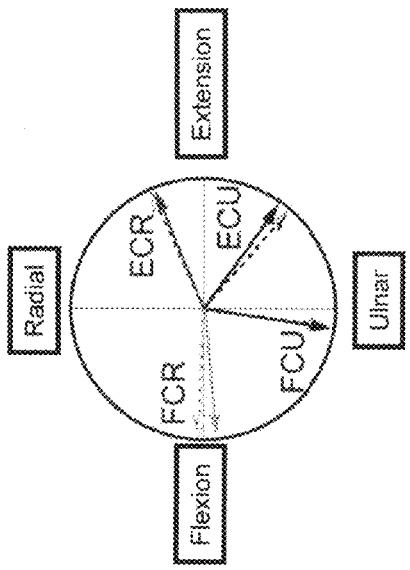
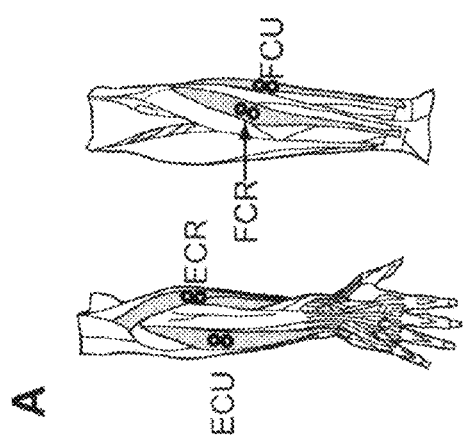
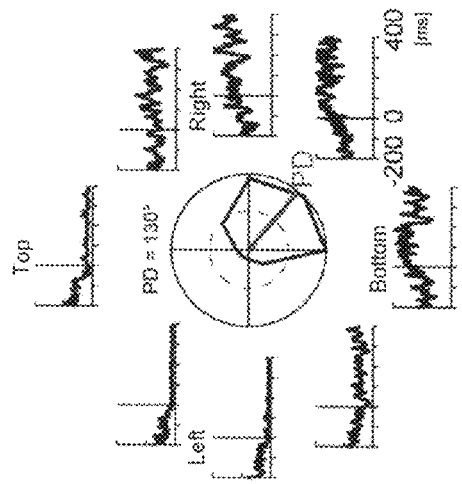
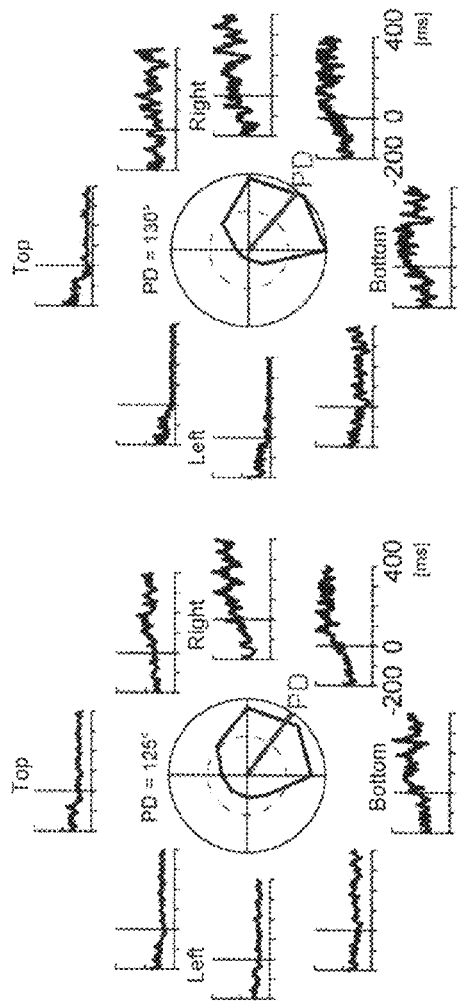

METHOD FOR IDENTIFYING AND EVALUATING PARALLEL MOTOR CONTROL FUNCTION IN THE BRAIN BASED ON ELECTROMYOGRAM SIGNALS

CROSS-REFERENCE TO RELATED APPLICATION

This application claims priority to Japanese Patent Application No. 2010-042301, filed on Feb. 26, 2010, the entire contents of which are hereby incorporated by reference.

FIELD OF THE INVENTION

The present invention relates to a method for identifying and evaluating parallel motor control function in the brain based on electromyogram (EMG) signals. Specifically, the present invention relates to a method for estimating the state of intracerebral motor controllers from muscle activities, using causal relationship between muscle activities and kinematics in joint movements.

BACKGROUND OF THE INVENTION

Recently, the present inventors have constructed a system for motor command analysis, evaluation and diagnosis that analyzes the motor commands of a subject during wrist joint movements (WO 2009/028221), and proved that it is possible to fully explain 2-DOF (degrees of freedom) motor components of the wrist joint based on the muscle activities of four prime movers of the wrist joint. Further, the present inventors have established a method for identifying causal relationship between muscle activities and movements in terms of the joint torque. Thus, it has become possible to quantitatively analyze abnormal movements in cerebellar diseases at the level of motor command. There are three major points in this invention.

First, it was possible to analyze motor commands by measuring as few as four wrist prime movers out of twenty and several muscles involved in wrist joint movements.

Secondly, it was possible to record the activities of the above four prime movers with electrodes attached on skin surfaces, without pain and non-invasively.

As a result, it has become possible to perform the analysis of motor commands (which was performed only at the laboratory level so far) simply and non-invasively in clinical practice.

Thirdly, the inventors have further invented an equation for identifying causal relationship between the thus simply and non-invasively recorded muscle activities of the above four prime movers and wrist movements in terms of the joint torque (WO 2009/028221).

Consequently, it has become possible to quantitatively analyze the involvement of individual muscles to abnormal movements in neurological disorder.

SUMMARY OF THE INVENTION

It is an object of the present invention to provide a system for evaluating motor control function in the brain from EMG data on wrist joint prime movers and data on the position, velocity and acceleration of the joint.

As a result of intensive and extensive researches toward solution of the above-described problem, the present inventors have approximated muscle activities and motor components in joint movements to joint torque, and focused attention on the viscosity coefficient and elastic coefficient in a movement equation during joint movements. By using the ratio between these two coefficients, the present inventors have succeeded in evaluating motor control function in the brain from muscle activities and movements.

The present invention relates to the following.

(1) A system for evaluating the motor control function in the brain of a subject from the electromyogram (EMG) data of joint prime movers and the data on the position, velocity and acceleration of the joint, wherein both of the data has been obtained by measuring a target-tracking movement performed by the subject with a motion measurement unit that tracks a moving target, the system comprising the following means (a) to (c):

(a) means for separating the frequencies of the EMG data and the frequencies of the data on the position, velocity and acceleration into a plurality of frequency components;

(b) means for determining the ratio of viscosity coefficient to elastic coefficient (B/K ratio) for each of the frequency components by applying the EMG data and the data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) means for evaluating the causal relationship between the target-tacking movement and the motor control function in the brain using the B/K ratio as an index.

(2) A program for evaluating the motor control function in the brain of a subject from the electromyogram (EMG) data of joint prime movers and the data on the position, velocity and acceleration of the joint, wherein both of the data have been obtained by measuring a target-tracking movement performed by the subject with a motion measurement unit that tracks a moving target, the program being for the purpose of bringing the following means (a) to (c) into practice:

(a) means for separating the frequencies of the EMG data and the frequencies of the data on the position, velocity and acceleration into a plurality of frequency components;

(b) means for determining the ratio of viscosity coefficient to elastic coefficient (B/K ratio) for each of the frequency components by applying the EMG data and the data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) means for evaluating the causal relationship between the target-tacking movement and the motor control function in the brain using the B/K ratio as an index.

(3) A computer-readable record medium storing the program of (2) above.

(4) A method of evaluating the motor control function in the brain of a subject from the electromyogram (EMG) data of joint prime movers and the data on the position, velocity and acceleration of the joint, wherein both of the data have been obtained by measuring a target-tracking movement performed by the subject with a motion measurement unit that tracks a moving target, the method comprising the following steps (a) to (c):

(a) a step of separating the frequencies of the EMG data and the frequencies of the data on the position, velocity and acceleration into a plurality of frequency components;

(b) a step of determining the ratio of viscosity coefficient to elastic coefficient (B/K ratio) for each of the frequency components by applying the EMG data and the data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) a step of evaluating the causal relationship between the target-tacking movement and the motor control function in the brain using the B/K ratio as an index.

(5). A method of processing the electromyogram (EMG) data of joint prime movers and the data on the position, velocity and acceleration of the joint obtained by measuring a target-tracking movement performed by a subject with a motion measurement unit that tracks a moving target, the method comprising the following steps (a) and (b):

(a) a step of separating the frequencies of the EMG data and the frequencies of the data on the position, velocity and acceleration into a plurality of frequency components; and (b) a step of determining the ratio of viscosity coefficient to elastic coefficient (B/K ratio) for each of the frequency components by applying the EMG data and the data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers.

(6) In the present invention, it is preferred that the EMG data are obtained by normalizing the magnitude of the EMG signals in proportion to the magnitude of joint torque, full-wave rectifying the thus normalized signals and filtering the resultant signals with a low-pass filter. With respect to the frequency components, two components of low frequency component and high frequency component may be given as examples. When the frequencies are separated into two frequency components, the boundary is preferably within the range from 0.3 to 0.8 Hz.

In the present invention, the subject is, for example, a patient with neurological disorder.

Further, in the present invention, the prime movers of a joint to be measured are, for example, arm muscles. Specific examples of such arm muscles include at least one selected from extensor carpi radialis (ECR), extensor carpi ulnaris (ECU), flexor carpi ulnaris (FCU) and flexor carpi radialis (FCR).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the recording of EMG signals from prime movers of the wrist joint.

FIGURE LEGENDS

Figure 1:
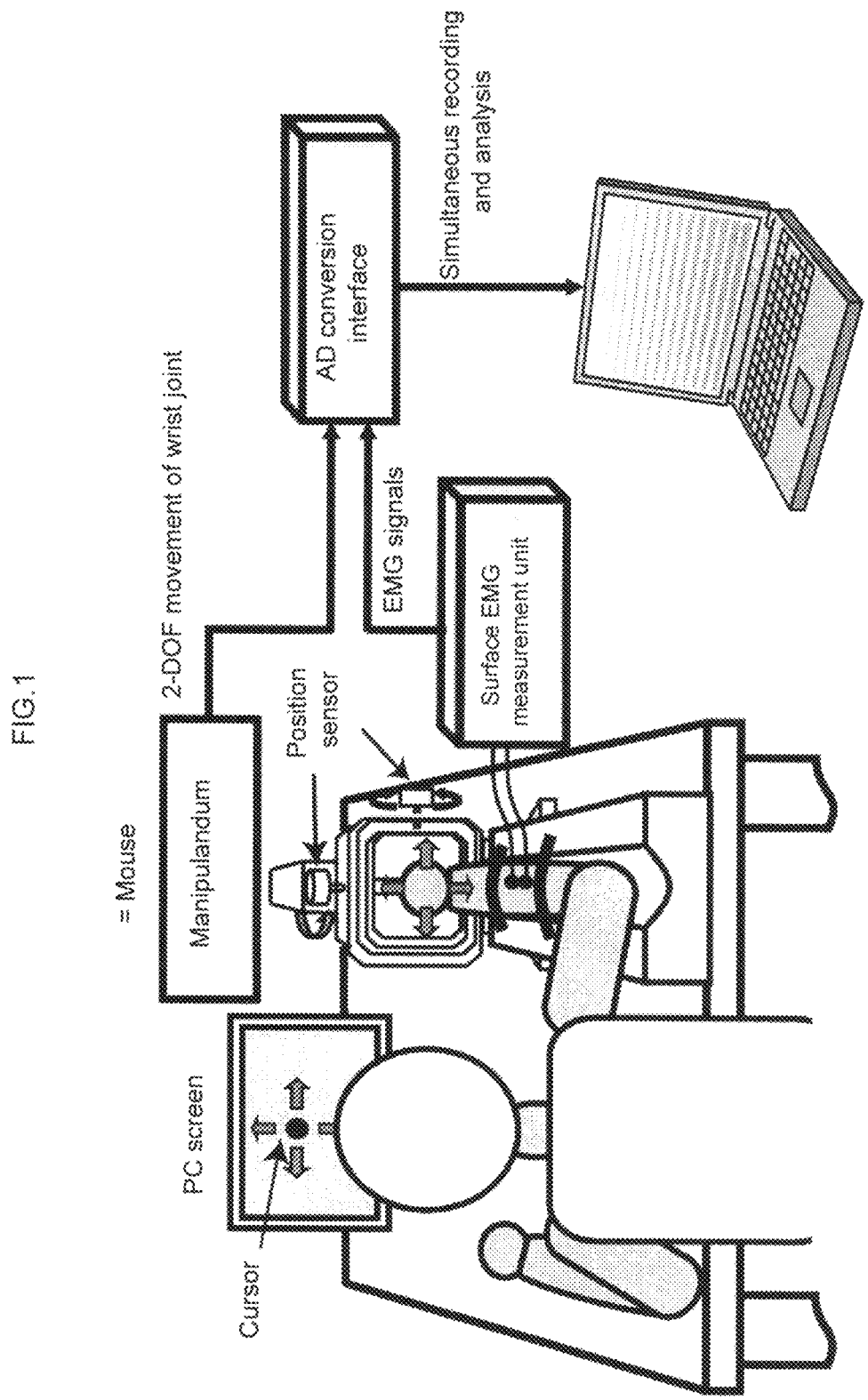
FIG. 1 shows an outline of the motor command analysis, evaluation and diagnosis method and the experimental setup.

100: the system of the present invention; 10: calculation member; 20: database

101: control member; 102: sending/receiving member; 103: input member, 104: output member 105: ROM; 106: RAM; 107: hard disc drive; 108: CD-ROM drive 111: internet connection; 120: CD-ROM

DETAILED DESCRIPTION OF THE INVENTION

Hereinbelow, the present invention will be described in detail. The following embodiment is an example for illustrating the present invention, which is not intended to limit the present invention. The present invention may be carried out in various embodiments without departing from the scope of the invention.

All of the literatures, laid-open patent publications, patent publications and other patent documents cited herein are incorporated herein by reference. The present specification incorporates the entire content of the specification and drawings of Japanese Patent Application No. 2010-042301 filed on Feb. 26, 2010 based on which the present application claims priority.

1. Outline

The present invention provides a novel method of estimating the motor control function or the state of motor controllers in the brain from muscle activities during movement, based on the causal relationship between muscle activities of a specific number of muscles that move a joint in joint movements and three components (position, velocity and acceleration) of the movements.

The method of the present invention is roughly divided into the following two steps:

(1) a step of identifying the causal relationship between muscle activities during target-tracking movement and a movement equation in terms of the joint torque, and intensively extracting the relationship between muscle activities and three components of the movement into the parameters of the movement equation determined at that time; and (2) a step of functionally evaluating the feedforward controller and feedback controller in the brain based on the above parameters.

In order to bring the above-described two steps into practice, the present invention provides a system for evaluating motor control function in the brain of a subject from the electromyogram (EMG) data of joint prime movers and the data on the position, velocity and acceleration of the joint, wherein both of those data have been obtained by measuring a target-tracking movement performed by the subject with a motion measurement unit that tracks a moving target (manipulandum). Further, the present invention provides a computer program for allowing a computer to bring such means into practice, and a method of function evaluation by bringing such means into practice.

The system or method of the present invention comprises the following means or step (a) to (c):

(a) means for or a step of separating the frequencies of the EMG data and the frequencies of the data on the position, velocity and acceleration into a plurality of frequency components;

(b) means for or a step of determining the ratio of viscosity coefficient to elastic coefficient (B/K ratio) for each of the frequency components by applying the EMG data and the data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where τ represents joint torque; θ represents joint angle (i.e. position of joint); $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) means for or a step of evaluating the causal relationship between the target-tacking movement and the motor control function in the brain using the B/K ratio as an index.

In the earlier patent application (WO 2009/28221), with respect to the three coefficients in the following terms acceleration $M\ddot{\theta}(t)$, velocity $B\dot{\theta}(t)$ and position $K\theta(t)$ (namely, M, B and K) in the equation, the values obtained in prior art by other researchers (Gielen and Houk 1984; Grey 1997; de Serres and Milner 1991; Milner and Cloutier 1998) were used as constants.

In the present invention, it is characteristic that analyses are made with B and K as variables. The reason for this is because the form of the equation represents mathematically the base conversion of a function and resembles a technique of analyzing a complicated function by decomposing into a trigonometric function in Fourier analysis. The method of the present invention is decisively different from the earlier method using constants, in a point that characteristics of the complicated entire muscle activity are transferred into the parameters B and K in the equation. By determining the ratio of B to K and using the ratio as an index, it is possible to know what the brain is "considering" when generating motor commands.

Theoretically, at least two types of this "considering" pattern are contemplated.

One is a simple position control of the joint, and the other is a hybrid control taking into account of both the position and the velocity of the joint. The former corresponds to a technological feedback controller and is the most primitive control. The latter corresponds to a technological feedforward controller and is higher control.

In order to put this theoretical idea into practice, the present inventors created concepts of control function designated "feedforward control" and "feedback control" as the second device, and designed a movement task in which motor commands generated from the brain are easily separated into feedforward control and feedback control. For this purpose, the present inventors used a movement task in which a subject tracks a target with a cursor that coordinates with the movement of his/her wrist, while the target moves on a specific trajectory smoothly and at a constant velocity.

Figure 2:
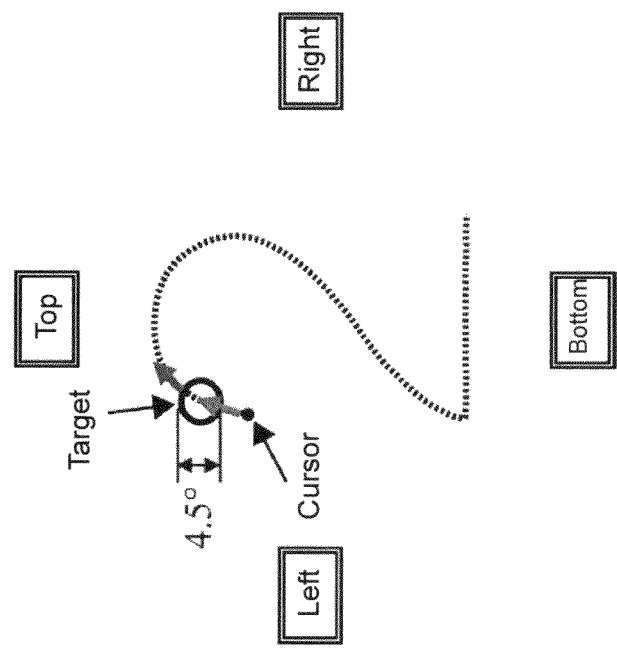
FIG. 2 shows a task of wrist joint movement that is a guide (numeric character "2") tracking movement.

For example, as shown in FIG. 1, evaluation of motor function according to the system described in WO 2009/28221 will be considered below. In the system described in WO 2009/28221, the right arm of a subject is fixed on the manipulandum and only the wrist is allowed to move. Electrodes are located on the arm to measure EMG signals from several muscles. On the PC screen, a target image (e.g., displayed as mark "○") that is designed to draw a pre-determined character or figure and a cursor that moves responding to the movement of the subject's wrist joint are displayed. Following the movement of the target image (mark "○"), the subject moves his/her wrist (wrist joint) with the manipulandum in such a manner that the cursor comes within the target image. For example, as shown in FIG. 2, following the movement of the target image drawing a numeric character "2", the subject moves the wrist joint to move the cursor in such a manner that the cursor comes within the target mark "○" and draws "2". (It should be noted that although numeric character "2" is indicated with a dotted line in FIG. 2, the dotted line is not displayed in actual trials.)

When EMG signals of specific muscles were measured as described above, the present inventors have examined the waveforms of the resultant EMG signals and focused attention on the following facts: that movements drawing a specific character in a predictive manner at a constant velocity generate loose waveforms and that movements correcting the position of the cursor so that it comes within the target image generate small waveforms. The present inventors have considered that the former corresponds to (i) frequencies reflecting in movements of drawing a character or the like of interest at a constant velocity and that the latter corresponds to (ii) frequencies reflecting in movements of dragging the cursor into the target image, and considered separation of EMG signals into these frequencies.

Before the trial using the manipulandum, subjects are allowed to practice several times. Therefore, the subjects are capable of predicting the movement of the cursor at the actual trial (e.g., they can know in advance that they should move the cursor in such a manner that it draws numeric character "2"). Accordingly, it can be said that the frequencies of (i) above are reflected as a function of controlling the prediction of movement in the brain, and the frequencies of (ii) above as a function of retaining the cursor at a proper position and correcting the positional deviation. In the present invention, this function of controlling the prediction of movement is defined as "feedforward control" and the function of retaining the cursor at the proper position as "feedback control". Organs in charge of these functions in the brain are designated "feedforward controller" and "feedback controller", respectively.

From what have been described so far, it is expected that feedforward motor commands appear as motor commands of low frequency component with smooth waveforms like the movement of the target, while feedback motor commands that correct positional deviation appear as motor commands of higher frequency component with small waveforms. As a result, feedforward motor commands and feedback motor commands can be easily separated by difference in frequency, and each of these two types of motor commands can be evaluated with B/K ratios.

As shown in Examples described later, the outputs of the two motor controllers are separated into feedforward motor commands of low frequency and feedback motor commands of high frequency, as expected. According to the present invention, a methodology of separating the two motor controllers and evaluating them individually has been established.

By the way, a hypothesis that the motor control center in the brain is divided into two modules was already proposed 60 years ago (Cybernetics of Wiener). However, this hypothesis has never been proved and remained persistently as a hypothesis.

On the other hand, the present invention has provided this long-standing hypothesis with experimental support for the first time and, at the same time, established a method in which the state of complicated motor control system in the brain is evaluated by resolving that state into a module of two virtual controllers ("feedforward controller" and "feedback controller"). For example, as organs in charge of feedforward control in the brain, the cerebellum and the like work dominantly; and as organs in charge of feedback control in the brain, the motor area of the cerebral cortex and the like work dominantly. Therefore, it is possible to analyze the function of intracerebral organs involved in movement depending on which control function is dominant or subordinate.

Further, with the system of the present invention, it is possible to obtain data easily without using expensive measuring instruments (such as MRI and MEG) and in a non-invasive manner which imposes less burden to patients with neurological disorder. Thus, the system of the present invention is suitable for bedside use. This point is a remarkable advantage in view of actual use.

2. Evaluation of Motor Control Function in the Brain

Those data obtained by trials (practices) using the above-described manipulandum may be analyzed after separation into components of the movement which the wrist performs in tracking a numeric character, character, figure, mark, etc. and components of the tension of the arm muscles required to perform the wrist movement.

Then, in the present invention, optimum approximation between components of the movement performed by motor organs and the muscle tension is attempted. The joint of a motor organ which is the target of analysis of kinematics is not particularly limited as long as it is monoarticular. For example, wrist joint, elbow joint, shoulder joint, hip joint, knee joint, foot joint and the like may be enumerated. The present invention may be applied to any of such joints. In the case of a monoarticular joint, it is possible to record the activities of several muscles as joint prime movers by means of surface EMG and then analyze the relation between the linear sum of the EMG signals and movement equations.

In the present invention, the wrist joint is preferably used because of easiness of trial practice. However, needless to say, other joints may also be used when a subject has a disorder in wrist movement. A motor organ or joint may be appropriately selected depending on the purpose of evaluation and the condition of the patient.

Hereinbelow, the present invention will be described taking the wrist joint as an example.

In the muscles which move the wrist joint (i.e., prime movers), muscles to be used in EMG measurement are not particularly limited. Preferably, extensor carpi radialis (ECR), extensor carpi ulnaris (ECU), flexor carpi ulnaris (FCU) and flexor carpi radialis (FCR) are used. One of these muscles or a combination of two or more of these muscles may be used for EMG measurement.

Components of the movement performed by the wrist may be separated into the following three components: the position, velocity and acceleration of the wrist joint. These values may be obtained in the actual trial. Then, wrist joint torque may be calculated with the movement equation (2) shown below:

$$\tau(t) = M\ddot{\theta}(t) + B\dot{\theta}(t) + K\theta(t) \tag{2}$$

where $\tau$ represents joint torque; $\theta$ represents joint angle (position); $\dot{\theta}$ represents the angular velocity of joint; $\ddot{\theta}$ represents the angular acceleration of joint; M represents the moment of inertia; B represents viscosity coefficient; and K represents elastic coefficient.

On the other hand, the muscle tension of arm muscles may be obtained from the EMG signals of the prime movers. When EMG signals are measured for a plurality of prime movers, the linear sum as shown in the following equation may be obtained by combining the individual EMG signals. Although EMG signals may be applied to the equation (3) shown below without any processing, it is preferred that the magnitude of the EMG signals is normalized in proportion to the magnitude of joint torque; the normalized EMG signals are full-wave rectified and then filtered with a low-pass filter. The term "normalization" means to adjust the magnitude of muscle activities generating a specific force so that the magnitude is constant between records of different subjects or between records of one same subject taken at different times. The term "full-wave rectification" means to calculate the absolute values of the recorded EMG signals. The term "low-pass filter" means convolution integral that converts full-wave rectified EMG waveforms to muscle tension.

$$\sum_{i=1}^{k} a_i T_i(t) \tag{3}$$

where $T_i(t)$ represents muscle tension; $a_i$ represents optimal approximation coefficient between joint torque and the linear sum of muscle tension; and k represents the number of prime movers.

By optimum approximation of the above-described kinematics and muscle tension, it is possible to show the kinematics and muscle tension in terms of wrist joint torque (equation (1) shown below).

$$\tau(t) = M\ddot{\theta}(t) + B\dot{\theta}(t) + K\theta(t) = \sum_{i=1}^{k} a_i T_i(t) \quad (1)$$

where τ represents joint torque; θ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers.

In the above-described equation (1), the most simple movement equation consists of the term of acceleration (1st term) alone. However, since the musculoskeletal system has viscosity element derived from muscles and element of spring derived from muscles and tendons, the term of velocity (2nd term) and the term of position (3rd term) are necessary. M, which represents the moment of inertia, is calculated from the volume of the hand of each subject actually measured individually regarding that a hand is a uniform sphere. The constants of proportionality of the terms of velocity and position (B and K) are designated "viscosity coefficient" and "elastic coefficient", respectively. $T_i(t)$ in the right-hand side represents muscle tension. $a_i$, which represents optimal approximation coefficient between joint torque and the linear sum of muscle tension, is determined taking into account of the direction of mechanical action of each muscle in human.

Here, the movement of the joint during a target-tracking movement (the movement is displayed by means of a cursor) includes smooth movement (low frequency movement) following the target and high frequency movement showing finely shaking waveforms. In the present invention, the inventors have analyzed this phenomenon from the velocity of the target-tracking movement (X component and Y component) and tangential velocity, and separated the movement into low frequency domain and high frequency domain. In the present invention, the number of frequency domains to be separated into is not particularly limited. The movement may be separated into two domains of low frequency and high frequency domains; or may be separated into three domains of low, middle and high frequency domains; or may be separated into four or more domains. In the present invention, it is preferable to separate the movement into two frequency domains (high frequency and low frequency). When the movement is separated into a plurality of frequency domains, the boundary frequency is selected from the range of 0.3 to 0.8 Hz. For example, when the movement is separated into two frequency domains, the boundary frequency is preferably 0.5 Hz.

In the target-tracking movement task, a subject tracks a target that is moving on a pre-determined trajectory at a constant velocity. If the subject is a healthy adult, he/she is capable of performing the tracking movement while predicting the movement of the target. Therefore, in motor commands of low frequency domain which coincides with the velocity of the target, it is possible to interpret that components of feedforward control (to track in a predictive manner the target moving on the known trajectory at the known velocity) are dominant. On the other hand, motor commands in high frequency domain are not correlated with the movement of the target and have no relation with feedforward control.

Figure 7:
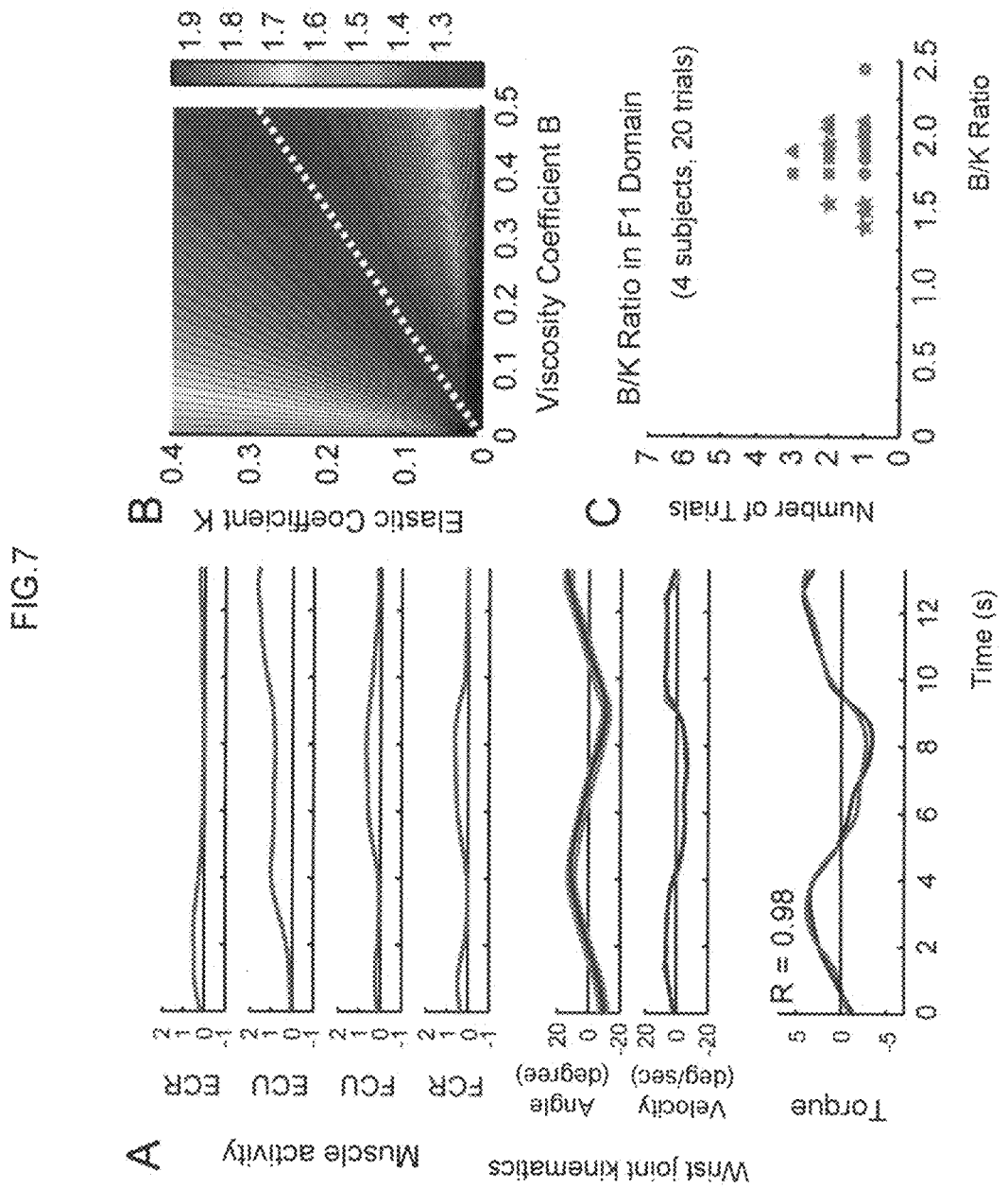
FIG. 7 shows identification of the causal relationship and B/K ratios in F1 domain (low frequency component) in the target tracking movement.
Figure 8:
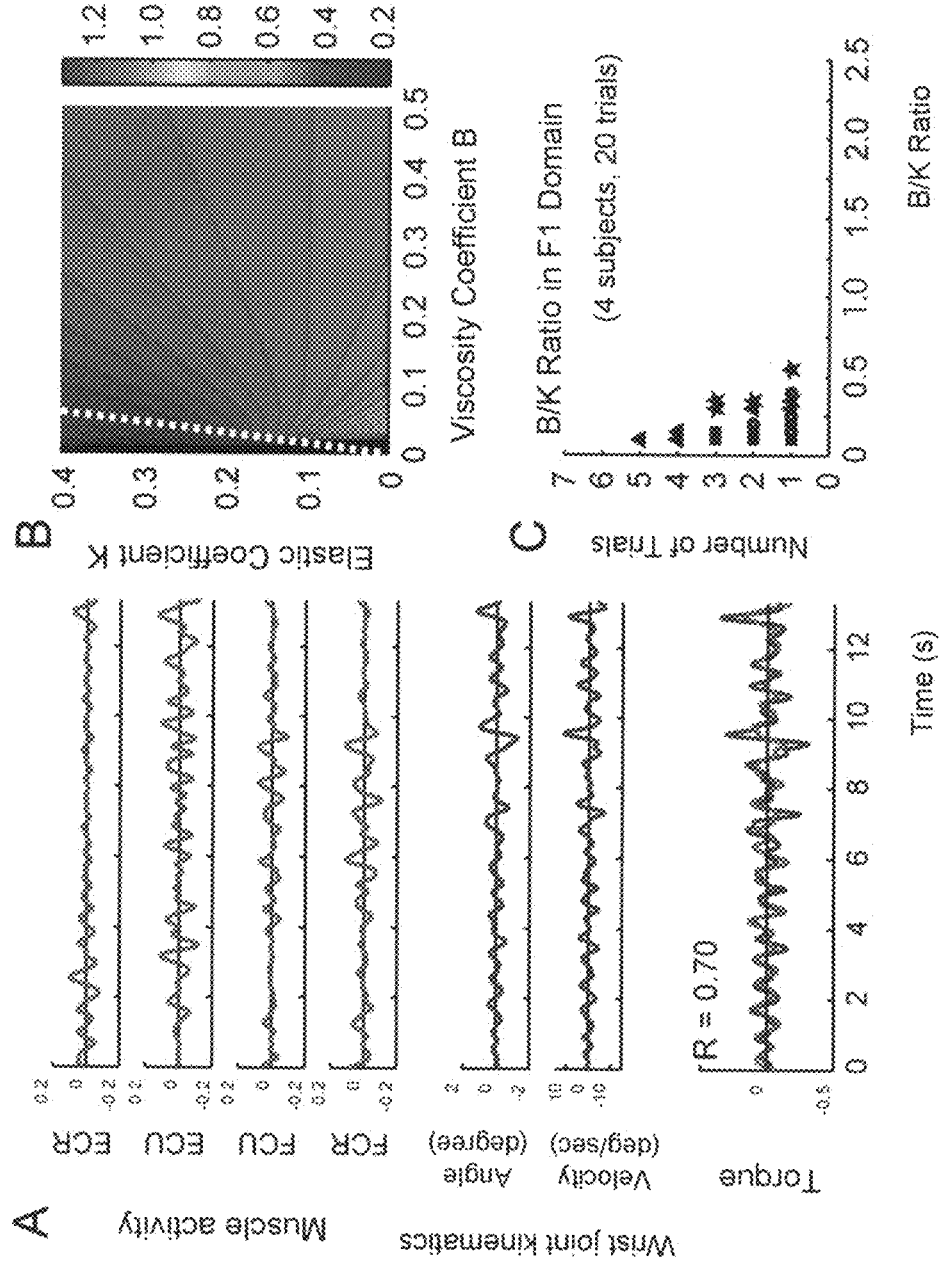
FIG. 8 shows identification of the causal relationship and B/K ratios in F2 domain (high frequency component) in the target tracking movement.

Subsequently, in the present invention, the ratio of B to K (B/K ratio) is determined with respect to the kinematics in low frequency domain and high frequency domain from the above-described equation (1). Since B and K can not be actually measured from trial practice using the manipulandum, optimum approximation of the equation (1) is performed for various combinations of B (0-0.5) and K (0-0.4) within a physiologically reasonable range, followed by evaluation of the goodness of approximation. Specifically, torque from movement in various combinations of B and K is calculated by the movement equation; the degree of optimum approximation between the resultant torque and the linear sum of muscle activities (muscle tension) is evaluated with the magnitude of correlation coefficient R (see FIG. 5). Examples of specific results are shown in FIG. 7B and FIG. 8B. From these Figures, it is clear that combinations of B and K which give optimum approximation are concentrated on a straight line that indicates a specific B/K ratio. From these results, it is possible to obtain B/K ratio simply without determining the absolute values of B and K which are difficult to obtain experimentally.

When the meanings of B and K are analyzed from the above-described movement equation (1), high viscosity coefficient B means that the linear sum of muscle activities is highly correlated with velocity components, indicating that motor commands for velocity control are contained abundantly in muscle activities. On the other hand, large elastic coefficient K means that the linear sum of muscle activities is highly correlated with position components, indicating that motor commands for position control are contained abundantly in muscle activities. Then, the present inventors have analyzed the difference of B/K ratio in these two components (position and velocity). The results revealed that the ratios of B and K are almost equal in the low frequency domain of movement component (FIG. 7B), indicating that muscle activities are deeply related with both position component and velocity component. On the other hand, K is dominant in the high frequency domain of movement component (FIG. 8B), indicating that muscle activities are deeply related with the position component of the wrist alone.

3. Two Parallel Motor Controllers in Target-Tracking Movement

To summarize what have been described so far, it is believed that motor commands in low frequency domain is the most important motor command for generating joint movement in real time that matches both the position and velocity of a target moving on a known trajectory at a known velocity to thereby respond to the demand of a task. On the other hand, it is believed that motor commands in high frequency domain play a feedback or subsidiary role of correcting the position of a cursor quickly online when the cursor is about to slip off from the center of the target.

Now, the two motor command components in the target-tracking movement will be examined from the viewpoint of motor controllers that generate such commands. Motor commands in low frequency domain contain both position and velocity components at a specific ratio and explicitly designate both position and velocity. On the other hand, motor commands in high frequency domain contain almost position components alone and do not designate velocity. Thus, the two motor commands are completely different in the mixing ratio of position component and velocity component; system of control is fundamentally different in these motor commands. Further, since there is no correlation between the two motor commands, it is strongly suggested that motor controllers generating these commands are independent from each other and work in parallel.

Figure 9:
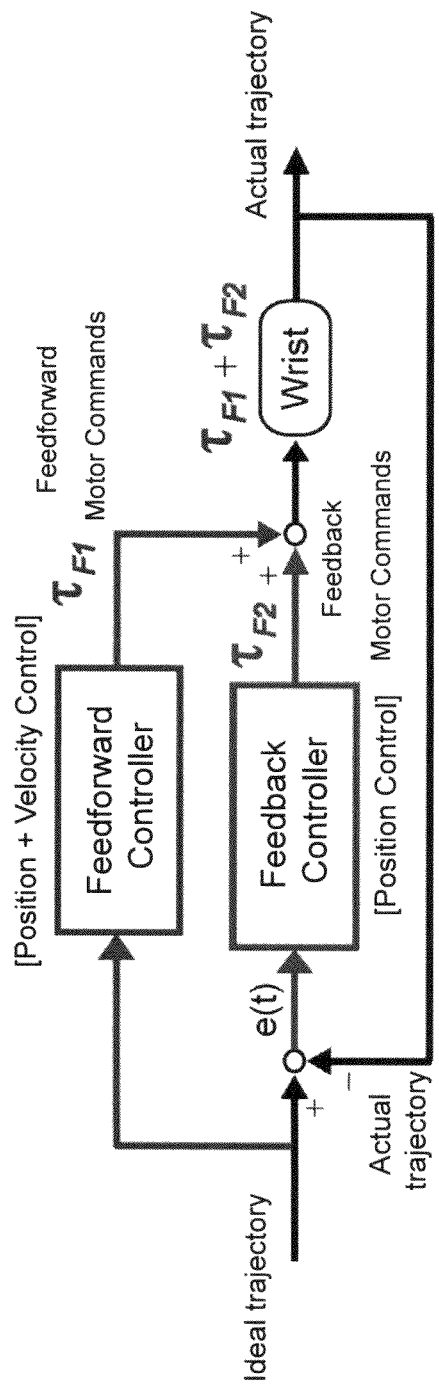
FIG. 9 shows a model of two parallel motor controllers in the target tracking movement.

When the mechanism of motor control in target-tracking movement is contemplated based on the above-described observation, a model as described in FIG. 9 is considered. In brief, there are two parallel controllers in target-tracking movement: (i) a feedforward controller which predicts the movement of a target that moves on a known trajectory at a known velocity and reproduces the same movement of the joint by designating both position and velocity; and (ii) a feedback controller which corrects only positional errors between the target and the joint (cursor). Outputs from these two controllers are added somewhere at the central nerve system up to motor neurons, and ultimately drive the same muscles.

Therefore, by calculating B/K ratio for each of the frequency components and comparing with normal patterns, it is possible to learn what disorder the patient (subject) has and which controller is damaged in what way. Such information is very important for doctors to understand the pathological condition of patients and make treatment plans and schedules.

Subjects applicable to the system of the present invention include, in addition to healthy persons, patients with neurological disorder. The system of the present invention may be used, for example, in treating neurological disorder. The treatment includes, for example, rehabilitation of the motor function of patients with neurological disorder. The neurological disorder includes, for example, a neurological disorder with movement disorder. Specifically, at least one disorder selected from the group consisting of Parkinson's disease, parkinsonian syndrome, Huntington's disease, athetosis, dystonia, cerebellar/spinal atrophy (including cerebellar disorder and spinocerebellar ataxia), multiple system atrophy, striatonigral degeneration, olivopontocerebellar atrophy, Shy-Drager syndrome, corticobasal degeneration, progressive supranuclear palsy, calcification of the basal ganglia, parkinsonism dementia syndrome, diffuse Lewy body disease, Alzheimer's disease, Pick's disease, Wilson's disease, multiple sclerosis, peripheral nerve disease, brain tumor and apoplexy may be preferable. Among all, Parkinson's disease, parkinsonian syndrome, cerebellar/spinal atrophy and appoplexy are especially preferable.

4. Evaluation System for Parallel Motor Controllers in the Brain

Figure 12:
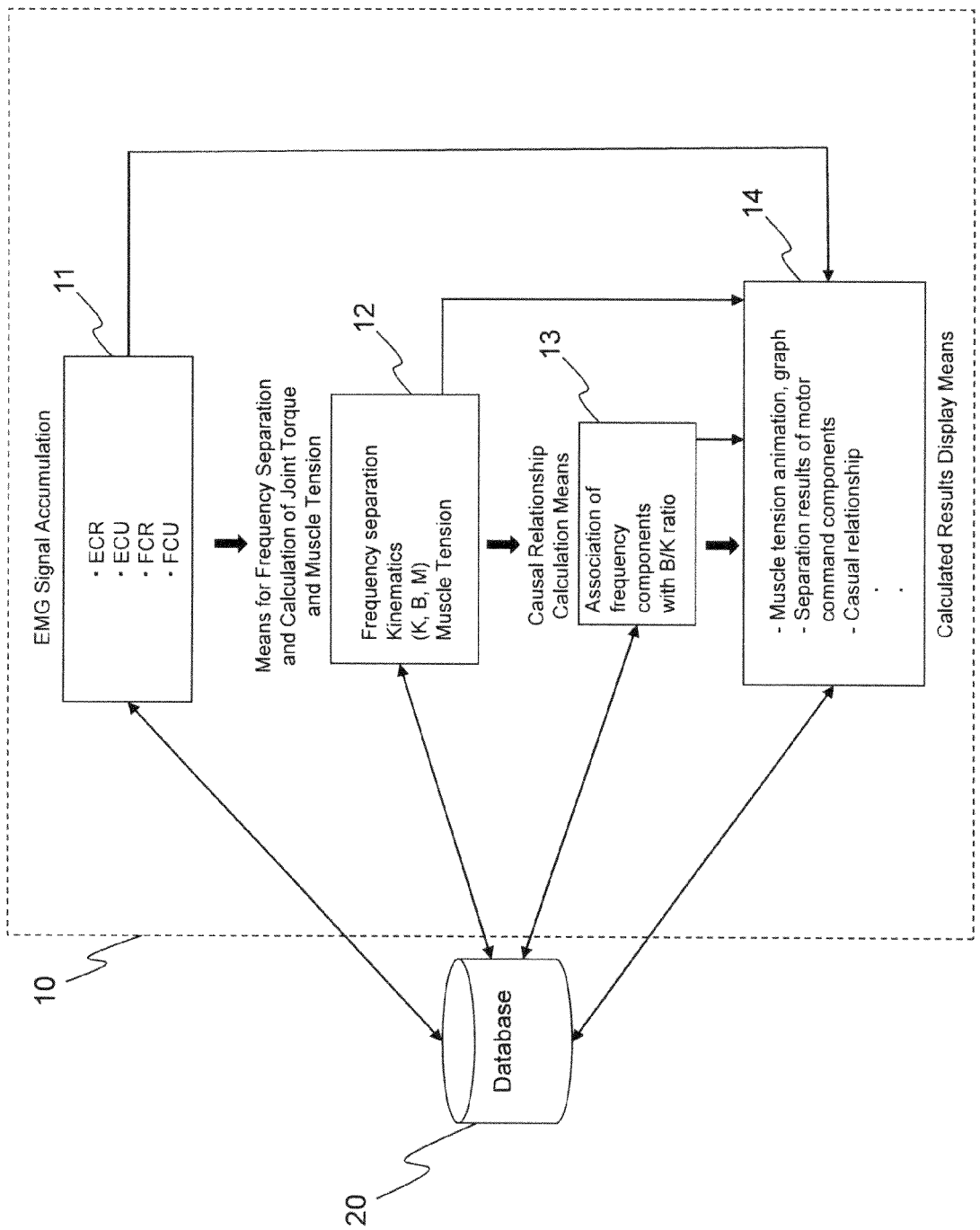
FIG. 12 is a block configuration diagram of the system of the present invention.

FIG. 12 is a configuration diagram of the system of the present invention. In FIG. 12, the system of the present invention is composed of a calculation means 10 and a database 20, and the calculation means 10 is equipped with (i) measured data accumulation means 11, (ii) means for separating frequencies and calculating joint torque and muscle tension 12, (iii) means for calculating causal relationship and (iv) means for displaying calculated results.

(i) Measured Data Accumulation Means 11

This is a means for accumulating the EMG data and data on the position of the joint and movement measured with a manipulandum. The accumulated data can be confirmed by graphs or tables.

(ii) Means for Separating Frequencies and Calculating Joint Torque and Muscle Tension 12

This is a means for performing frequency separation of data from the measured data accumulation means 11 or the database 20, and for calculating joint torque and muscle tension for each of the separated frequency components using the movement equation. With this means, it is possible to calculate the position, velocity and acceleration of the joint (which are components of movement) according to the data from the manipulandum.

The calculation formula for joint torque (2) is as described below.

$$\tau(t) = M\ddot{\theta}(t) + B\dot{\theta}(t) + K\theta(t) \quad (2)$$

where τ represents joint torque; θ represents joint angle (position); $\dot{\theta}$ represents the angular velocity of joint; $\ddot{\theta}$ represents the angular acceleration of joint; M represents the moment of inertia; B represents viscosity coefficient; and K represents elastic coefficient.

The calculation formula for the linear sum of muscle tension (3) is as described below.

$$\sum_{i=1}^{k} a_i T_i(t) \quad (3)$$

where $T_i(t)$ represents muscle tension; $a_i$ represents optimal approximation coefficient between joint torque and the linear sum of muscle tension; and k represents the number of prime movers.

The linear sum in the above formula is subjected to optimum approximation with the joint torque calculated by (ii) means for calculating joint torque.

(iii) Causal Relationship Calculation Means 13

This is a means for calculating the causal relationship between muscle activities and kinematics, the relationship between velocity components of the wrist and frequency components obtained from EMG data in target-tracking movement, or ratios of feedforward control and feedback control, based on the separated frequency components, calculated B/K ratios and the number of trials.

(iv) Calculated Results Output Means 14

This is a means for outputting the measured data, the calculated joint torque, kinematics and muscle tension, B/K ratios and causal relationship. This means displays the joint torque and muscle tension calculated by (ii) above in the form of animation or graph. At the same time, this means is also capable of displaying the causal relationship and B/K ratios calculated by (iii) above in graphs.

(v) Data Accumulation Means

Measured data and calculated results which have been input are associated with each other and stored in the database 20 as a data accumulation means.

The stored calculation conditions and calculated results may be readable from the database 20, or the accumulation means 11, the calculation means 12 and 13, and the calculated results display means 14.

5. Computer Program

Figure 13:
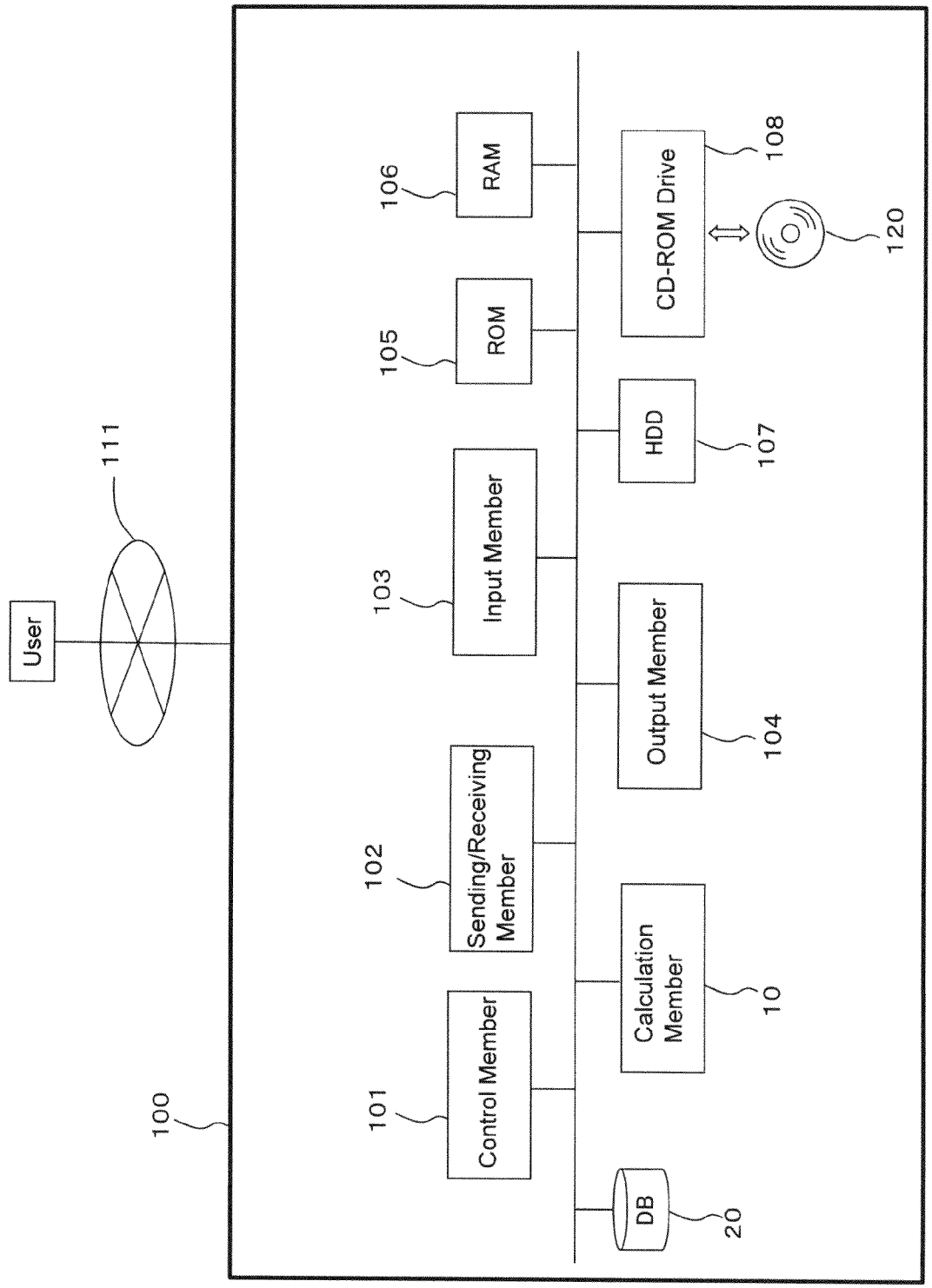
FIG. 13 is a detailed configuration diagram of a system for running the program of the present invention.

Means for allowing a computer to run the program of the present invention are shown in a configuration diagram in FIG. 13.

FIG. 13 is a detailed configuration diagram of a system 100 for running the program of the present invention. In FIG. 13, the system 100 is equipped with the calculation means 10 and the database (hereinafter, abbreviated to "DB") 20 shown in FIG. 12, and further comprises a control member 101, a sending/receiving member 102, an input member 103, an output member 104, a ROM 105, a RAM 106, a hard disc drive (HDD) 107 and a CD-ROM drive 108.

The control member 101 is a central processing unit such as CPU or MPU, and controls the activities of the entire system 100. In particular, the control member 101 controls the communication of the sending/receiving member 102, or retrieves displayed data (such as motor control process and the result thereof) using the stored data in DB 20.

The sending/receiving member 102 performs data sending/receiving to and from a user terminal, based on commands from the control member 101. The user terminal may be connected via an internet connection 111. The user terminal or the internet connection is used mainly when pre-measured and stored EMG data and movement data or data supplied from a remote user are analyzed. The sending/receiving member 102 sends to the calculation member 10 those parameters and calculation formulas which are necessary for calculating joint torque and muscle tension.

The input member 103 is composed of keyboard, mouse, touch panel, etc., and is operated when inputting parameters and updating the contents of DB 20. The output member 104 is an LCD (liquid crystal display) or the like, and converts the code data from the control member 101 into display data each time when DB 20 is updated, thus performing display processing. ROM 105 stores processing programs for the system 100. RAM 106 tentatively stores those data which are necessary for the system 100 to perform processing. HDD 107 stores programs, etc., and retrieves the stored programs or data and stores them in RAM 106, for example, based on commands from the control member 101. CD-ROM drive 108 retrieves the programs, etc. stored in CD-ROM 120 and writes them in RAM 106 or the like, based on commands from the control member 101. It is also possible to use a rewritable CD-R, CD-RW or the like as record medium instead of CD-ROM 120. In that case, a drive for the CD-R or CD-RW is equipped instead of the CD-ROM drive 108. Alternatively, a medium such as DVD, MO, flash memory stick, etc. may be used and a drive corresponding thereto may be equipped.

Figure 14:
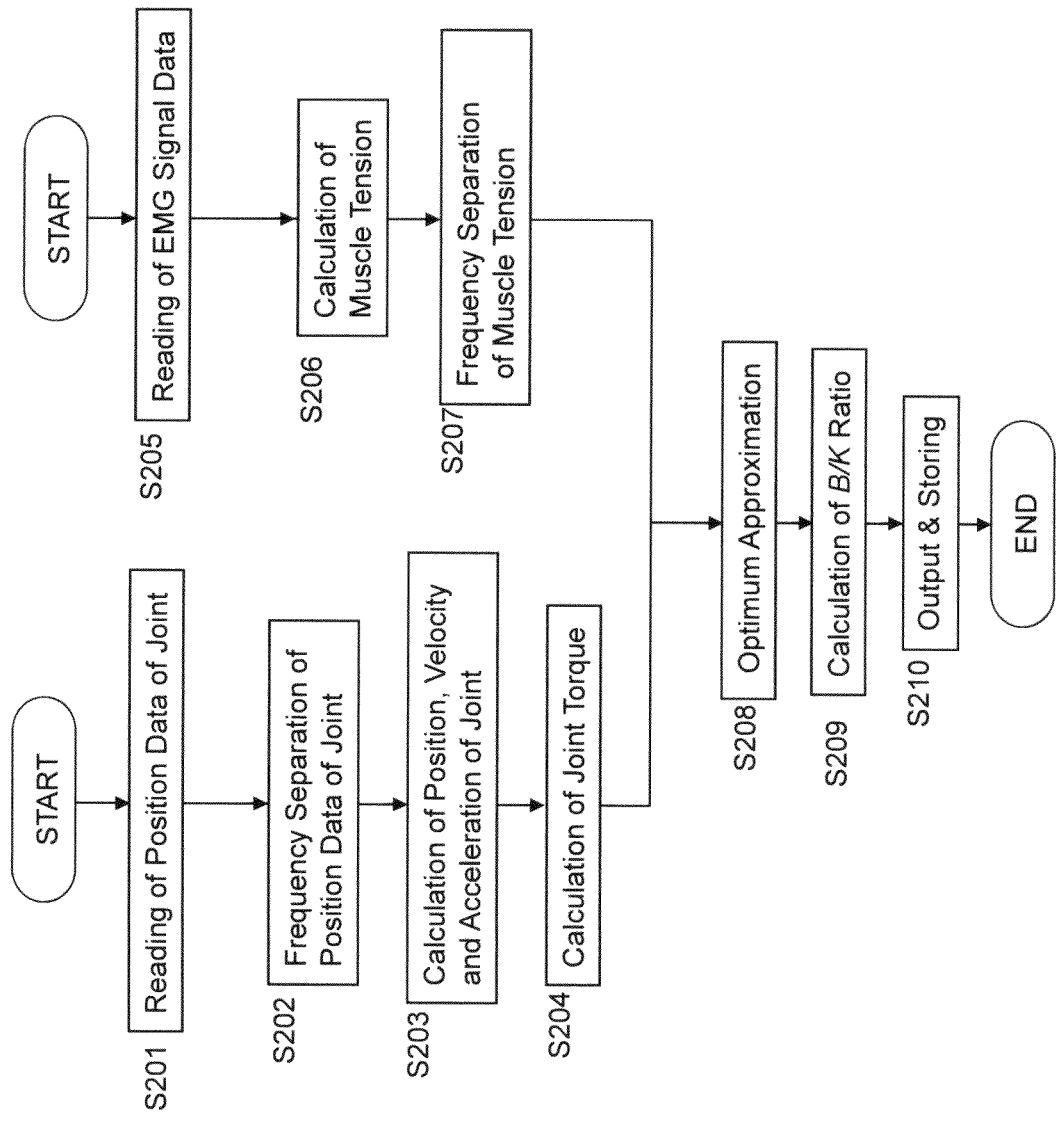
FIG. 14 is a flow chart illustrating the behaviors of the program of the present invention.

FIG. 14 is a flow chart illustrating the behaviors of the program of the present invention.

The program of the present invention performs the following (a) and (b) based on the input measured data:
(a) calculation by the means for separating frequencies and calculating joint torque and muscle tension 12, and
(b) calculation by the causal relationship calculation means 13.

Activation of such calculation may be achieved by commands from the control member 101.

Calculations may be performed, for example, in the following order:
(i) To read data on the position of the wrist joint from the measured data accumulation means 11 or the database 20 (S201).
(ii) To separate the data on the position of the wrist joint into a plurality of frequency components by the means for separating frequencies and calculating joint torque and muscle tension 12 (S202).
(iii) To calculating the position, velocity and acceleration (kinematics) of the wrist joint for each of the frequency components of the position data by the means for separating frequencies and calculating joint torque and muscle tension 12 (S203).
(iv) To calculating the position, velocity and acceleration (kinematics) of the wrist joint for each of the frequency components of the position data by the means for separating frequencies and calculating joint torque and muscle tension 12 (S204).
(v) On the other hand, to read EMG signal data from the measured data accumulation means 11 or the database 20 (S205).
(vi) To determine muscle tension from EMG signals by the means for separating frequencies and calculating joint torque and muscle tension 12 (S206) (see FIG. 4).
(vii) To separate muscle tension into a plurality of frequency components by the means for separating frequencies and calculating joint torque and muscle tension 12 (S207).
(viii) To perform optimum approximation between the calculated joint torque and the linear sum of muscle tension for each of the frequency components by the means for separating frequencies and calculating joint torque and muscle tension 12 (S208) (see FIG. 5).
(ix) To identify the causal relationship between muscle activities and kinematics for various combinations of B and K by the above procedures (iii) to (viii) for each of the frequency components by the causal relationship calculation means 13, to thereby calculate optimum B/K ratio (S209).
(x) To output the calculated joint torque, kinematics and muscle tension, B/K ratio and causal relationship by the calculated results output means 14 (S210). Examples of displayed results are shown in FIGS. 4, 6, 7 and 8.
(xi) To store the calculated results sequentially in the data accumulation means DB 20 (S210).

It should be noted here that the above-described steps (i) to (iv) and steps (v) to (vii) may be programmed in such a manner that either one group of steps are performed in advance and the other group of steps follow. Alternatively, both groups may be programmed in such a manner that they are performed simultaneously.

Calculated results are stored sequentially in the database that is a data accumulation means.

6. Computer-Readable Record Medium

The program of the present invention can be written in a language such as C language, Java, Perl, Fortran, Pascal, etc. and is designed to be compatible with cross-platform. Therefore, this software is capable of running on Windows™ 95/98/2000/XP/Vista/7, Linux, UNIX™, Macintosh, etc.

The program of the present invention may be stored in a computer-readable record medium or a computer-connectable memorizing means. A record medium or memorizing means for computer containing the program of the present invention is also included in the present invention. Specific examples of record medium or memorizing means include, but are not limited to, magnetic media (such as flexible disc and hard disc), optical media (such as CD and DVD), magnetooptical media (such as MO and MD) and flash memory.

Hereinbelow, the effect of the present invention will be described more specifically with reference to the following Examples. These Examples are not intended to limit the scope of the present invention.

EXAMPLE 1

1. Experimental Apparatus

The present invention relates to a method of analyzing the motor control function of a subject based on the causal relationship between muscle activities as motor commands in various joint movements of the subject and the resultant joint movement of the subject. The present invention used a motor command analysis, evaluation and diagnosis system using wrist joint movements (WO 2009/028221). An outline and experimental setup of the motor command analysis, evaluation and diagnosis system used in the present invention are shown in FIG. 1.

A subject is seated in front of a PC screen displaying a cursor and a target with his/her right forearm being supported with an armrest, and operates a wrist joint manipulandum with his/her right hand. Two degrees of freedom (2-DOF) movements of the wrist joint are measured with two position sensors and reflected on movements of the cursor (black dot, 2 mm in diameter) on the PC screen. The target is displayed as a circle; its diameter (1 cm) corresponds to a 4.5° movement of the wrist joint; and its position serves as a guide for wrist joint movements.

2. Subjects and Experimental Task

Four healthy adults without any history of neurological disorder (age: 44-63 years) participated in the experiment as subjects. The subjects were requested to perform, as experimental task, wrist movements of tracking a target that is moving at a constant velocity (mean velocity: 6.2 deg/sec) (FIG. 2). The starting point of movement is located upper left on the monitor (X=−10°, Y=8°). First, when a circular target is displayed upper left on the monitor, the subjects move their wrist joint to retain the cursor (coordinating with the wrist joint) at the starting point. Three seconds thereafter, the target begins to move at a constant velocity drawing a trajectory of numeric character "2". The subjects move their wrist joint to hold the cursor within the moving target as much as possible. Each subject was allowed to practice this task 2-3 times so that he/she can understand the task fully. Subsequently, real trial was performed 5 times for each subject.

3. Recording

During the movement task, surface EMG signals were recorded simultaneously from four wrist prime movers (extensor carpi radialis (ECR), extensor carpi ulnaris (ECU), flexor carpi ulnaris (FCU) and flexor carpi radialis (FCR)) involved in the position of the wrist joint (X, Y) and wrist joint movements. The velocity and acceleration of the wrist joint were determined by differentiating position signals once and twice, respectively, and used for estimating the joint torque of the wrist joint.

Recording of EMG signals was performed as follows: skin surface potential was induced bipolarly using a pair of Ag—AgCl surface electrodes and EMG signals were sampled at 2 kHZ and 12 bit. The electrodes were 5 mm in diameter and attached to the skin surface along the muscle fiber in such a manner that the distance between the electrodes is 10 mm. FIG. 3A shows the muscles measured and approximate positions of the electrodes. In the record of EMG signals with surface electrodes, identification of the recorded muscles is important and decides the experimental accuracy. In order to evaluate the reliability of this identification in the experimental system of the present invention, recording of surface EMG (FIG. 3C, left panel) and direct recording with wire electrodes from the muscles immediately below the surface electrodes (FIG. 3C, right panel) were performed simultaneously on one subject for four muscles. Then, the results were compared.

As a result, waveforms from the two recordings were highly consistent with each other. Further, the directions of peak of muscle activities (preferred direction; PD) calculated based thereon were almost consistent (FIG. 3B). Thus, effectiveness of muscle identification and recording of surface EMG signals was confirmed.

4. Processing of EMG Signals

Figure 4:
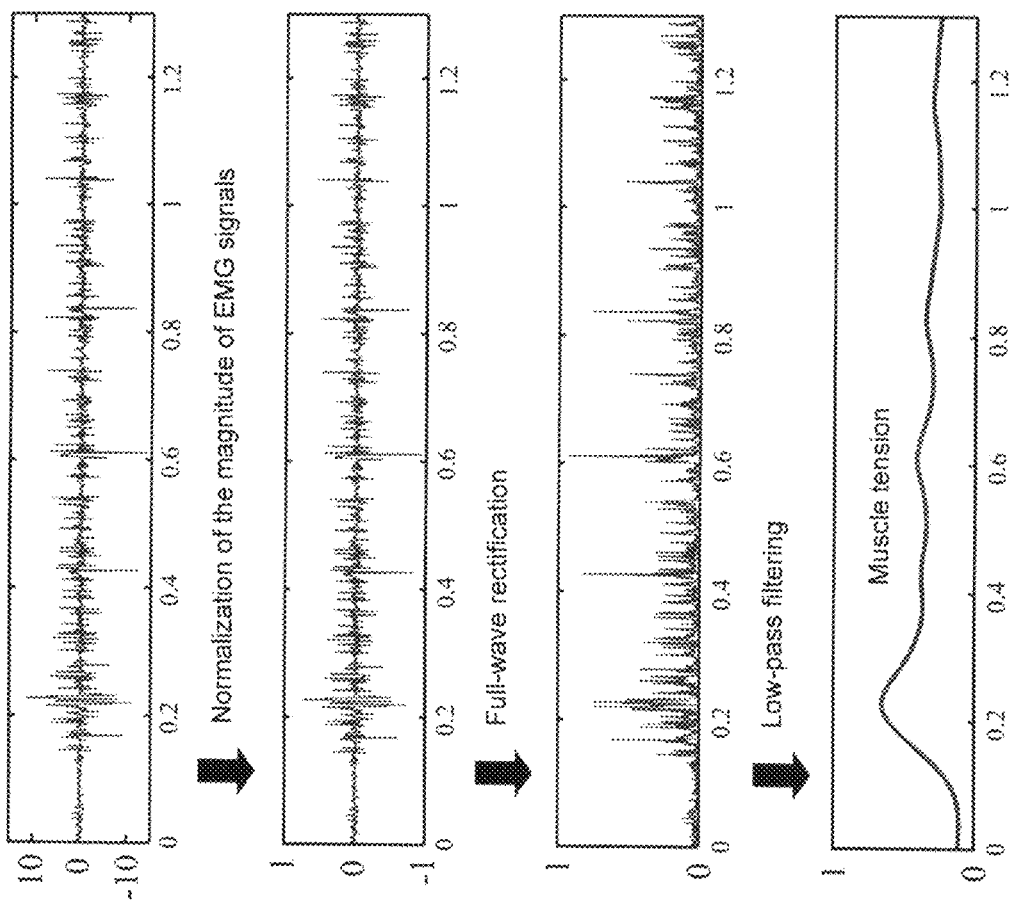
FIG. 4 shows the processing of EMG signals and muscle tension.

Motor commands from the central nerve system induce action potential from spinal motor neurons to muscles, generating muscle contraction. The action potential of this muscle contraction measured on skin surface is surface EMG (hereinafter, abbreviated to "EMG"), and the magnitude of EMG signals is proportional to muscle tension (Basmajian and De Luca, 1985). However, recorded EMG signals vary in absolute value depending on dermal resistance or relative positioning of electrode on muscles, and thus raw EMG signals are not suitable for quantitative analysis. Therefore, the present inventors normalized the magnitude of EMG signals in proportion to the magnitude of joint torque, as shown in FIG. 4. Briefly, the magnitude of muscle activities generating a specific force was adjusted so that the magnitude is constant between different subjects, or between records of the same subject taken at different times. Subsequently, the normalized EMG signals were full-wave rectified (calculation of absolute values of the recorded EMG signals). Finally, muscle tension was determined by filtering the rectified EMG signals with a low-pass filter of a second order (cut-off frequency: 3 Hz). The term "low-pass filter" means convolution integral that converts full-wave rectified EMG waveforms to muscle tension.

Figure 5:
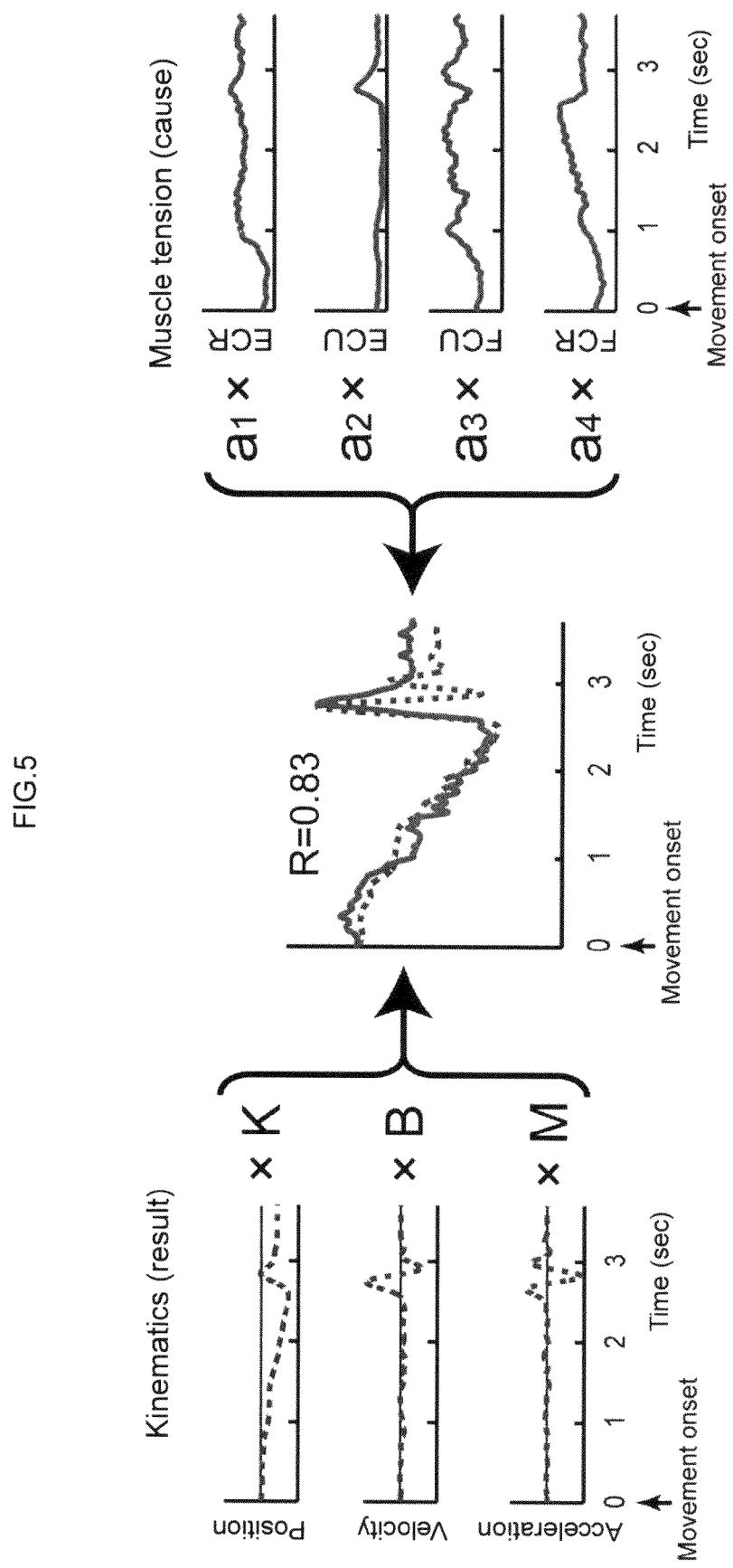
FIG. 5 shows identification of the causal relationship between muscle activities and movements in terms of the joint torque.

5. Method of Identifying Causal Relationship between Muscle Activities and Kinematics, and B/K Ratio In the present invention, causal relationship between muscle activities and kinematics of the wrist joint in wrist joint movements was identified in terms of joint torque, as shown in FIG. 5. Subsequently, the present inventors examined to which component of the kinematics the muscle activities (cause) is deeply related from the magnitudes of velocity coefficient B and elastic coefficient K in the equation determined at the time of identification.

With respect to specific calculation, joint torque (hatched line shown in the middle panel of FIG. 5) was calculated from the movement equation in the middle side of equation (1) below, and then optimum approximated with the linear sum of the four muscle activities (muscle tension) (the right-hand side of equation (1)) (solid line shown in the middle panel of FIG. 5). This means that causal relationship between muscle activities and movement equation was identified in a joint torque-mediated manner.

$$\tau(t) = M\ddot{\theta}(t) + B\dot{\theta}(t) + K\theta(t) = \sum_{i=1}^{k} a_i T_i(t) \quad (1)$$

In the above equation, $\tau$ represents wrist joint torque; $\theta$ represents joint angle; $\dot{\theta}$ and $\ddot{\theta}$ represent the angular velocity and angular acceleration of joint, respectively.

M (the moment of inertia) was calculated from the volume of the hand of each subject actually measured individually regarding that a hand is a uniform sphere. $T_i(t)$ represents muscle tension free of the effect of gravity, and was determined by subtracting the muscle tension at the starting point during postural maintenance from the muscle tension determined from EMG signals during movement. $a_i$, which represents optimal approximation coefficient between joint torque and the linear sum of muscle tension, was determined taking into account of the direction of mechanical action of each muscle in human.

Since actually measured values of B and K during wrist movement are not available, optimum values were determined based on the values of B and K during rest (Gielen and Houk 1984; Grey 1997; de Serres and Milner 1991; Milner and Cloutier 1998) within a physiologically reasonable range [B: 0-0.5 Nms/rad; K: 0-0.4 Nm/rad]. In particular, in the case of wrist joint, the moment of inertia M (constant) is so small compared to B and K that the term of acceleration can be virtually disregarded. Therefore, since it is difficult to specify the absolute values of B and K, the present inventors have decided to evaluate their values in terms of B/K ratio. As a result, it has become possible to avoid the technically difficult problem of determining the absolute values of B and K. This point is also a technically important invention.

6. Two Components in Target-Tracking Movement

When the movement of the wrist joint (cursor) during target-tracking movement was observed, finely shaking movements of higher frequency were seen in addition to smooth movements following the target. This phenomenon was analyzed from the velocity (X component, Y component) and tangenial velocity of the target-tracking movement (FIG. 6A). As seen from FIG. 6A, velocity change of the wrist joint (solid line) is shaking finely around the smooth velocity change of the target (hatched line). This shaking phenomenon was observed in common in all the subjects. Then, frequency analysis of velocity components was performed for every subject (FIG. 6B).

The results revealed a tendency that velocity components are separated into a low frequency domain and a high frequency domain with a boundary of about 0.5 Hz.

Therefore, velocity components were separated into "F1 domain" of lower frequencies (0-0.5 Hz) and "F2 domain" of higher frequencies (0.5-3 Hz) (FIG. 6C).

In the lower frequency F1 domain (FIG. 6C(a)), the velocity components of the wrist joint (solid line) completely consistent with the velocity of the target (hatched line) alone were left. On the other hand, in the higher frequency F2 domain (FIG. 6C(b)), the velocity components which are shaking at a frequency of about 1.4 Hz and are not correlated with the movement of the target were mainly left.

These results can be interpreted as follows. Briefly, in the target-tracking movement task, subjects track a target that is moving on a pre-determined trajectory at a constant velocity. If the subject is a healthy adult, he/she can fully understand the movement of the target with 2-3 times of practice, and can perform the tracking movement at a success rate of almost 100% predicting the movement of the target. Therefore, it can be interpreted that motor commands of F1 domain (which is consistent with the velocity of the target) mainly contain those components of feedforward control that tracks the target moving on a known trajectory at a known velocity in a predictive manner. On the other hand, it is believed that motor commands of higher frequency of F2 domain are not correlated with the movement of the target and have no relation with feedforward control.

Figure 6:
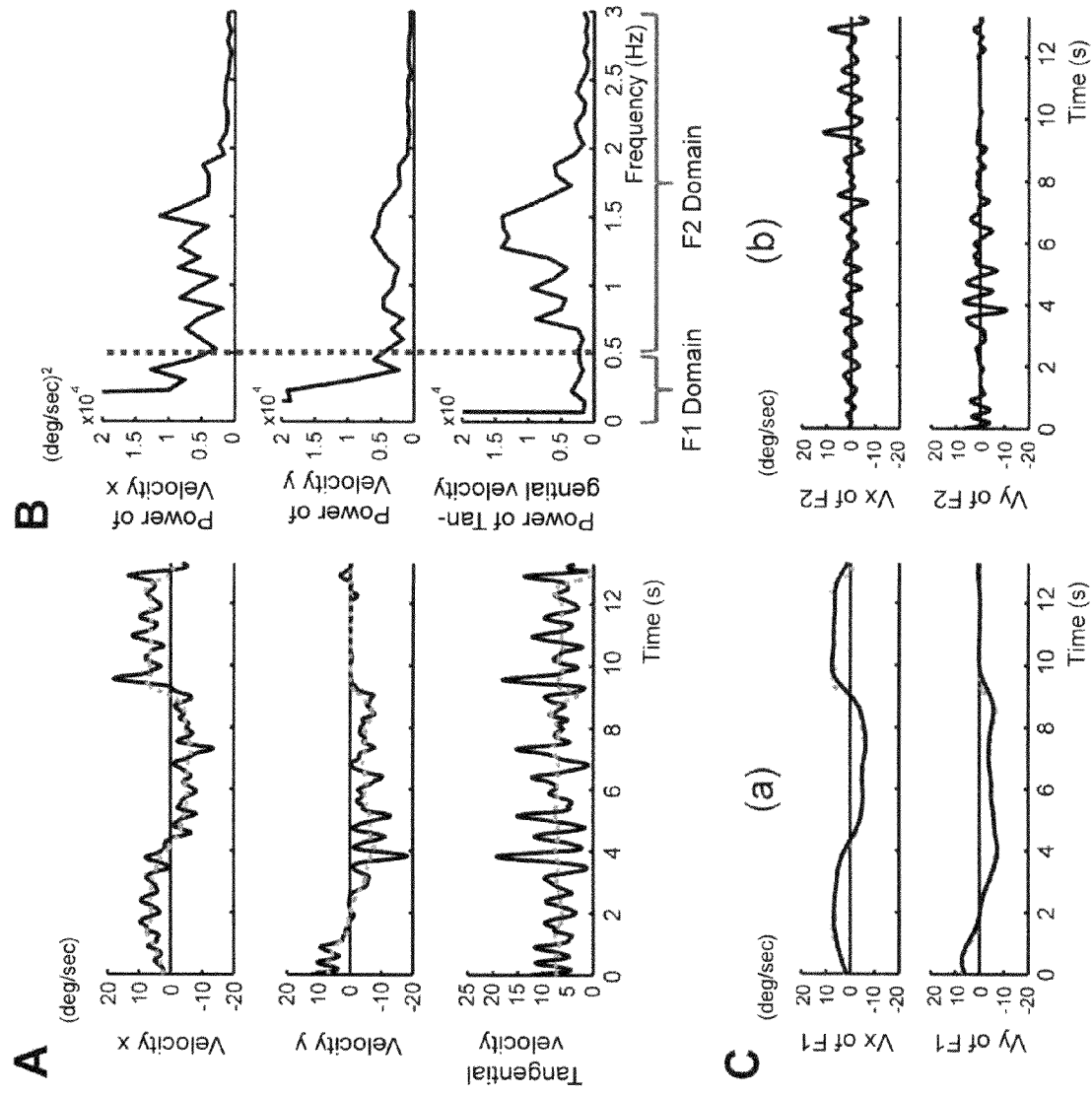
FIG. 6 shows separation of two motor command components in the target tracking movement.

7. Identification of Causal Relationship for Two Components of Target-Tracking Movement As indicated in FIG. 6, the two components in the target-tracking movement definitely play functionally different roles. Then, the functional significance of each of these components was examined by calculating a B/K ratio that gives optimum approximation between motor commands and wrist joint movements for each component.

First, individual components of 4 muscle tensions and kinematics were separated into F1 domain (0-0.5 Hz) and F2 domain (0.5-3 Hz), followed by optimum approximation between the above-described muscle activities and wrist joint movements using the movement equation (1).

Examples of optimum approximation in F1 domain and F2 domain are shown in FIG. 7A and FIG. 8A, respectively.

For both components (see the bottom row in FIG. 7A and FIG. 8A), it can be seen that wrist joint torque is approximated at a high correlation (F1 domain: R=1.98; F2 domain: R=0.70) with muscle tension. Although the correlation in F2 domain is somewhat low, the reason is presumed that muscle activities in this domain is less than in F1 domain in healthy subjects and S/N ratio is inferior. Surprisingly, B/K ratios in the two motor command components revealed good contrast. B/K ratio is high in lower frequency F1 domain (FIGS. 7B and 7C) and very low in higher frequency F2 domain (FIGS. 8B and 8C).

When the meanings of B and K are analyzed from the movement equation, high viscosity coefficient B means that the linear sum of muscle activities is highly correlated with velocity components, indicating that motor commands for velocity control are contained abundantly in muscle activities. On the other hand, large elastic coefficient K means that the linear sum of muscle activities is highly correlated with position components, indicating that motor commands for position control are contained abundantly in muscle activities. Then, based on this interpretation, the present inventors have analyzed the difference of B/K ratio in the two components. The results revealed that muscle activities are deeply related with both position component and velocity component in F1 domain where the ratios of B and K are almost equal. On the other hand, muscle activities are deeply related with the position component of the wrist alone in F2 domain where K is dominant.

EXAMPLE 2

Evaluation of Motor Function Based on Two Parallel Motor Controllers

1. Clinical Application of Two Parallel Motor Controllers 1: Cerebellar Diseases The method of the present invention has resolved the chaotic pathological condition of neurological disorders into a module of two motor controllers whose functional meanings are clear, to thereby enable evaluation of motor function that is easy to interpret intuitively. The biggest utility value of the method of the present invention resides in this point.

Figure 10:
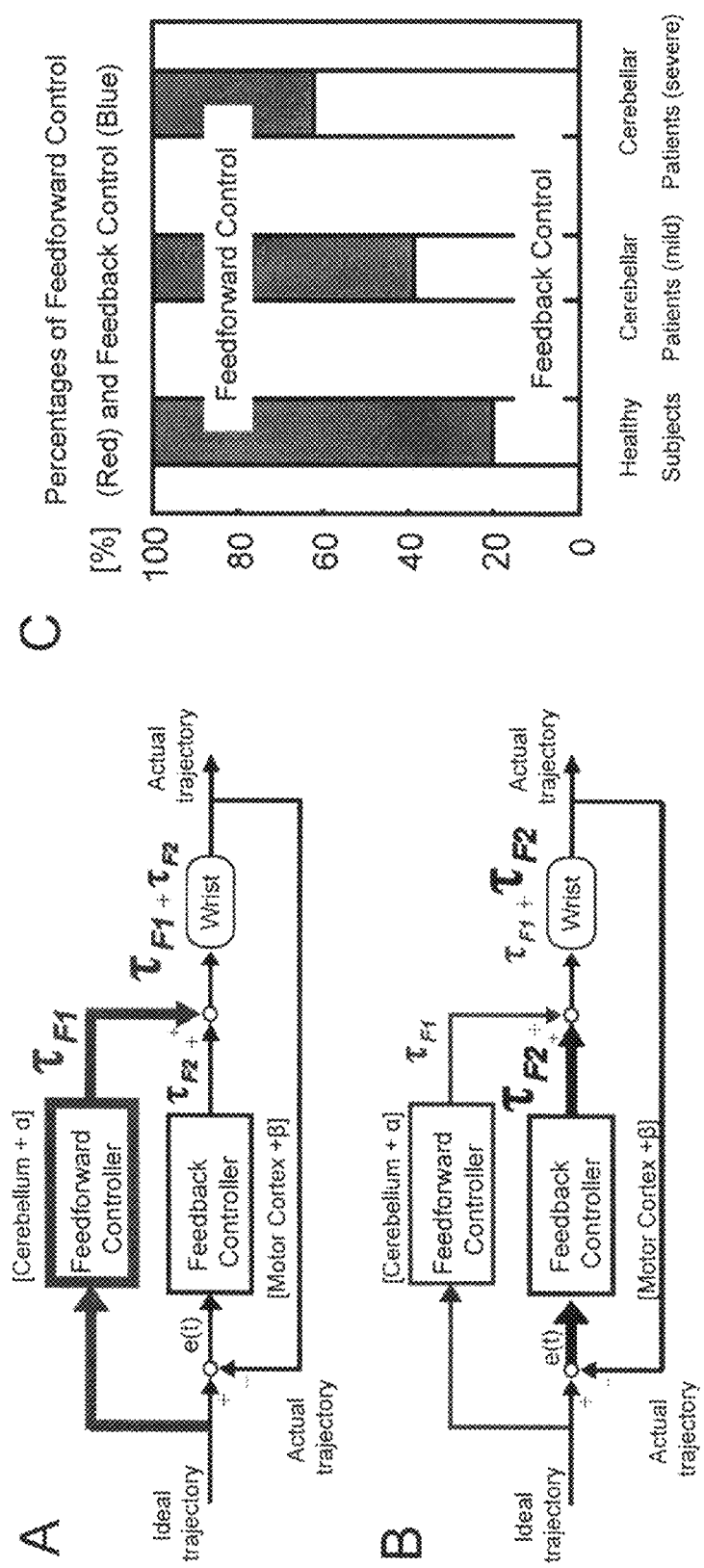
FIG. 10 shows application of the present invention to assessment of pathological conditions of cerebellar ataxia.

For example, since a healthy person can perform movements making full use of cerebellar feedforward controller, he/she is expected to use feedback controller subsidiarily (FIG. 10A). However, a cerebellar patient is expected to use the feedback controller of the mortor area frequently in order to compensate the damage to cerebellar feedforward controller (FIG. 10B).

This expectation was supported by real data as shown in FIG. 10C.

This Figure compares healthy subjects with cerebellar patients as to in what percentages motor commands of feedforward control (dark color) and motor commands of feedback control (white color) are contained.

As expected, while healthy subjects perform movements mainly depending on feedforward controller, it was found that the percentage of feedforward control decreases inversely correlated with the severity of disorder in cerebellar patients and that feedback control is used more by these patients.

As described above, with the method of the present invention, it is possible to analyze clearly what effect (qualitative) and to what extent (quantitatively) neurological disorder is giving on the motor control system of the brain from the viewpoint of two motor controllers which are feedforward control and feedback control.

2. Clinical Application of Two Parallel Motor Controllers 2: Appoplexy

Figure 11:
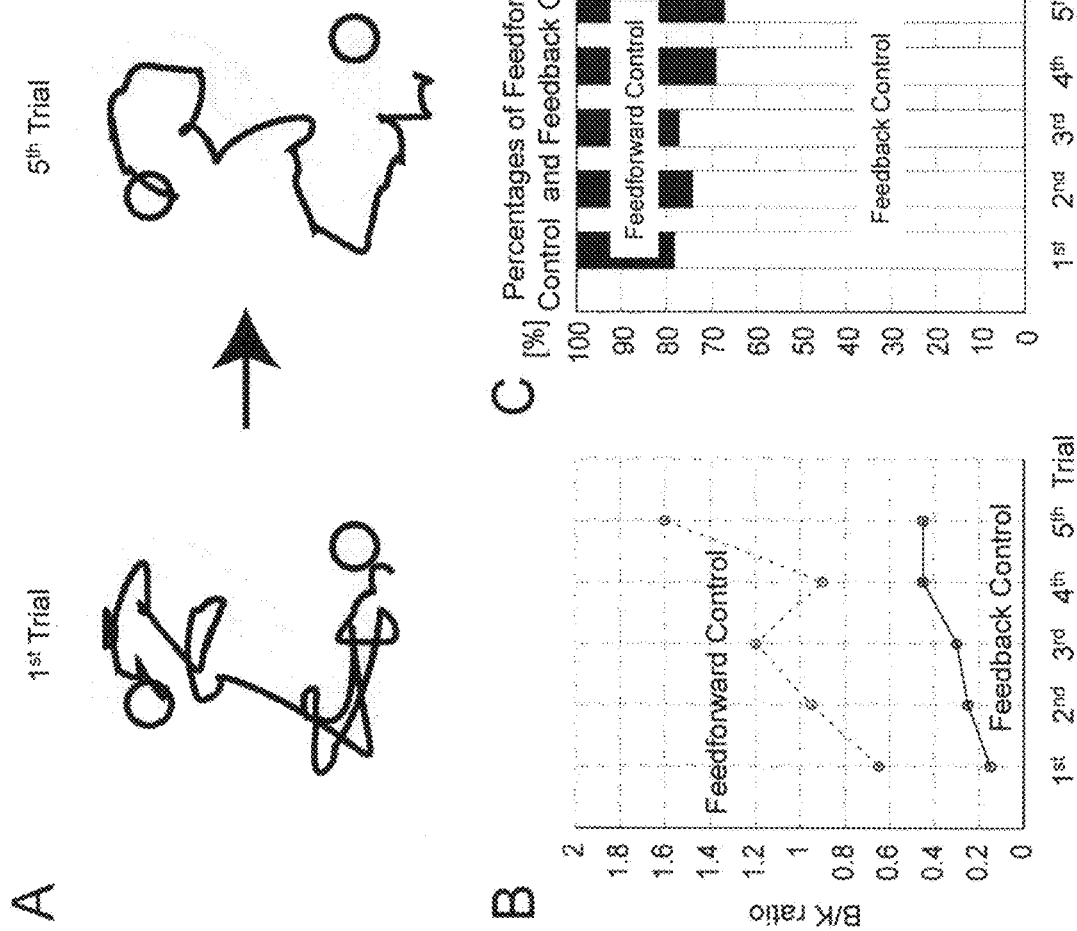
FIG. 11 shows application of the present invention to feasibility assessment of apoplexy patients' rehabilitation.

With application of the method of the present invention, the state of complicated motor control system in the brain in apoplexy patients was quantified using as indexes two virtual motor controllers (i.e., feedforward controller and feedback controller); feasibility of rehabilitation was assessed; and the process of recovery from paralysis was described. FIG. 11A shows the trajectories of the wrist joint of 1st trial and 5th trial, when an apoplexy patient performed the target-tracking movement 5 times repeatedly. At the 1st trial, the movement is continuously disturbed, and the intended movement is not achieved at all. However, a definite improvement is observed at the 5th trial, and the shape of numeric character "2" can be seen. In response to this improvement in trajectory, the percentage of motor commands for feedforward control increases as trials are repeated (FIG. 11C). At the same time, the B/K ratio of motor commands in the same domain increases. It is understood that the patient's intention to perform a smooth velocity control is reflected in motor commands (FIG. 11B). These results demonstrate that the motor controllers of at least a part of paralyzed patients retain flexible learning ability.

3. Clinical Significance of Motor Function Evaluation Based on Two Parallel Controllers According to the method of the present invention, it has become possible to quantitatively evaluate the state of two motor controllers in the brain simply and non-invasively without recording signals in the brain. Such a method of evaluation of function has never existed in the category of conventional evaluation of rehabilitation and neurological diagnosis and evaluation methods.

Due to recent advancement in diagnostic imaging technology using such as MRI, now it is common sense that the position and expansion of lesions in the brain are evaluated down to the millimeter with an accuracy of a small-sized nucleus. Localization diagnosis by imaging is one of the tidemarks. However, methodology that evaluates the functional significance of lesions has not progressed much for the recent 100 years, modestly speaking. Methods of quantitative analysis of movement developed recently are mere quantification of the description of movement. Such methods have been completely unable to make evaluation on motor controllers in the brain. The method of the present invention is the only one system capable of evaluating motor controllers in the brain functionally and quantitatively.

EFFECT OF THE INVENTION

According to the present invention, there is provided a system for evaluating motor control function in the brain. With the system of the present invention, it is possible to obtain data easily without using expensive measuring instruments (such as MRI and MEG) and in a non-invasive manner which imposes less burden to patients with neurological disorder. Thus, the system of the present invention is suitable for bedside use. Therefore, the system of the present invention is extremely useful as a test method for selecting treatment methods or the like for patients with neurological disorder.

The method of the present invention is the only one system capable of evaluating motor controllers in the brain functionally and quantitatively, and is industrially extremely useful.

What is claimed is:

1. A system for evaluating the motor control function in the brain of a subject from the electromyogram (EMG) data of joint prime movers and the data on the position, velocity and acceleration of the joint, wherein both of said data have been obtained by measuring a target-tracking movement performed by the subject with a motion measurement unit that tracks a moving target, said system comprising a computer, configured using a program or software, to perform the following steps (a) to (c):

(a) separating the frequencies of said EMG data and the frequencies of said data on the position, velocity and acceleration into a plurality of frequency components;
   (b) determining the ratio of viscosity coefficient to elastic coefficient (B/K ratio) for each of said frequency components by applying said EMG data and said data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\ddot{\theta}$ represents the angular velocity of joint; $\dot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and
   (c) evaluating the causal relationship between the target-tacking movement and the motor control function in the brain using said B/K ratio as an index.

2. The system according to claim 1, wherein the EMG data are obtained by normalizing the magnitude of the EMG signals in proportion to the magnitude of joint torque, full-wave rectifying the thus normalized signals and filtering the resultant signals with a low-pass filter.

3. The system according to claim 1, wherein said frequency components consist of two components of low frequency component and high frequency component.

4. The system according of claim 3, wherein the boundary between said two frequency components is within the range from 0.3 to 0.8 Hz.

5. The system according to claim 1, wherein said subject is a patient with neurological disorder.

6. The system according to claim 1, wherein said joint prime movers are arm muscles.

7. The system according to claim 6, wherein said arm muscle is at least one selected from extensor carpi radialis (ECR), extensor carpi ulnaris (ECU), flexor carpi ulnaris (FCU) and flexor carpi radialis (FCR).

8. A non-transitory computer-readable record medium storing a program for evaluating the motor control function in the brain of a subject from the electromyogram (EMG) data of joint prime movers and the data on the position, velocity and acceleration of the joint, wherein both of said data have been obtained by measuring a target-tracking movement performed by the subject with a motion measurement unit that tracks a moving target, said program being for the purpose of bringing the following steps (a) to (c) into practice:

(a) separating the frequencies of said EMG data and the frequencies of said data on the position, velocity and acceleration into a plurality of frequency components;
   (b) determining the ratio of viscosity coefficient to elastic coefficient (B/K ratio) for each of said frequency components by applying said EMG data and said data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\ddot{\theta}$ represents the angular velocity of joint; $\dot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) evaluating the causal relationship between the target-tacking movement and the motor control function in the brain using said B/K ratio as an index.

9. A method for evaluating the motor control function in the brain of a subject from the electromyogram (EMG) data of joint prime movers and the data on the position, velocity and acceleration of the joint, wherein both of said data have been obtained by measuring a target-tracking movement performed by the subject with a motion measurement unit that tracks a moving target, said method comprising using a program or software on a computer or system, configured using the program or software, to perform the following steps (a) to (c):

(a) separating the frequencies of said EMG data and the frequencies of said data on the position, velocity and acceleration into a plurality of frequency components;

(b) determining the ratio of viscosity coefficient to elastic coefficient (B/K ratio) for each of said frequency components by applying said EMG data and said data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers; and (c) evaluating the causal relationship between the target-tacking movement and the motor control function in the brain using said B/K ratio as an index.

10. A method of processing the electromyogram (EMG) data of joint prime movers and the data on the position, velocity and acceleration of the joint obtained by measuring a target-tracking movement performed by the subject with a motion measurement unit that tracks a moving target, said method comprising using a program or software on a computer or system, configured using the program or software, to perform the following steps (a) and (b):

(a) separating the frequencies of said EMG data and the frequencies of said data on the position, velocity and acceleration into a plurality of frequency components;

(b) determining the ratio of viscosity coefficient to elastic coefficient (B/K ratio) for each of said frequency components by applying said EMG data and said data on the position, velocity and acceleration to the following movement equation (1):

$$\tau(t) = M\ddot{\theta}(t) + B\dot{\theta}(t) + K\theta(t) = \sum_{i=1}^{k} a_i T_i(t) \quad (1)$$

where $\tau$ represents joint torque; $\theta$ represents joint angle; $\dot{\theta}$ represents the angular velocity of joint; $\ddot{\theta}$ represents the angular acceleration of joint; M represents the moment of inertia; B represents viscosity coefficient; K represents elastic coefficient; $T_i(t)$ represents muscle tension; $a_i$ represents optimal approximation coefficient between joint torque and the linear sum of muscle tension; and k represents the number of prime movers.

* * * * *